United States Patent
Williams et al.

(10) Patent No.: US 7,232,549 B2
(45) Date of Patent: Jun. 19, 2007

(54) APPARATUS FOR CONTROLLING THE FREE SURFACE OF A LIQUID IN A WELL PLATE

(75) Inventors: Roger O. Williams, Paradise Valley, AZ (US); Humphrey W. Chow, Cupertino, CA (US); Charles A. Reichel, Fremont, CA (US)

(73) Assignee: EDC Biosystems, Inc., Milpitas, CA (US)

( * ) Notice: Subject to any disclaimer, the term of this patent is extended or adjusted under 35 U.S.C. 154(b) by 0 days.

(21) Appl. No.: 11/186,150

(22) Filed: Jul. 20, 2005

(65) Prior Publication Data

US 2005/0281712 A1    Dec. 22, 2005

Related U.S. Application Data

(62) Division of application No. 10/010,366, filed on Nov. 5, 2001, now abandoned.

(51) Int. Cl.
    *B01L 3/02*     (2006.01)
(52) U.S. Cl. .................... 422/100; 422/102; 347/46
(58) Field of Classification Search ............. 422/99, 422/100, 102; 347/19, 20, 44, 46, 47, 84; 436/180
See application file for complete search history.

(56) References Cited

U.S. PATENT DOCUMENTS

| | | | | | |
|---|---|---|---|---|---|
| 4,748,461 | A | * | 5/1988 | Elrod | 347/46 |
| 5,629,724 | A | * | 5/1997 | Elrod et al. | 347/10 |
| 5,631,678 | A | * | 5/1997 | Hadimioglu et al. | 347/46 |
| 5,669,971 | A | * | 9/1997 | Bok et al. | 118/300 |
| 5,736,100 | A | * | 4/1998 | Miyake et al. | 422/64 |
| 5,821,958 | A | * | 10/1998 | Lim | 347/46 |
| 5,912,679 | A | * | 6/1999 | Takayama et al. | 347/10 |
| 6,010,316 | A | * | 1/2000 | Haller et al. | 417/322 |
| 6,103,199 | A | * | 8/2000 | Bjornson et al. | 422/100 |
| 6,612,686 | B2 | * | 9/2003 | Mutz et al. | 347/46 |
| 6,666,541 | B2 | * | 12/2003 | Ellson et al. | 347/46 |
| 6,719,449 | B1 | * | 4/2004 | Laugharn et al. | 366/127 |
| 2003/0049862 | A1 | * | 3/2003 | He et al. | 436/180 |
| 2003/0085952 | A1 | | 5/2003 | Williams et al. | |

* cited by examiner

*Primary Examiner*—Jill Warden
*Assistant Examiner*—Dwayne K. Handy
(74) *Attorney, Agent, or Firm*—Donald J. Pagel

(57) ABSTRACT

Devices useful in liquid transfer applications and in particular, devices for controlling the free surface of a source liquid in acoustic liquid ejection systems are disclosed. The devices advantageously maintain a source liquid to be transferred at a constant height and reduce disturbances formed in the liquid due to droplet ejection. In one variation, a well plate includes a plurality of wells each having a capillary. Source liquid in a well moves up the capillary due to capillary action and arrives at a certain height. The height arrived at remains constant despite the source liquid depleting from the well during the ejection process. The capillary can be separately joined or integral with the well plate. An acoustic wave emitter positioned adjacent to the well plate emits a focused acoustic beam that causes at least some of the liquid in the capillary to be ejected.

19 Claims, 9 Drawing Sheets

APPARATUS FOR CONTROLLING THE FREE SURFACE OF A LIQUID IN A WELL PLATE

This application is a division of application Ser. No. 10/010,366, filed Nov. 5, 2001 now abandoned, which is incorporated herein by reference.

TECHNICAL FIELD

This invention relates to apparatuses useful in liquid dispensing and in particular, to an apparatus for controlling the free surface of a source liquid in acoustic liquid dispensing.

BACKGROUND

Many methods for the precision transfer and handling of fluids are known and used in a variety of commercial and industrial applications. The biotechnology and biopharmaceutical industries are particularly relevant examples of industries requiring ultra-pure fluid handling and transfer techniques. Current biotechnological screening and manufacturing methods also require high throughput to efficiently conduct screening of compound libraries, synthesis of screening component, and the like.

Various current fluid transfer methods require contacting the fluid with a transfer device, e.g., a pipette, a pin, a needle or the like. Such contact methods dramatically increase the likelihood of contamination. Many biotechnology procedures, e.g., polymerase chain reaction (PCR), are extremely sensitive and can tolerate essentially no contamination. Accordingly, non-contact liquid transfer techniques are desirable.

Acoustic liquid dispensing is an example of a suitable non-contact dispensing technique that can eject droplets without contaminating the source liquid. Typically, such ejectors require focussing acoustic energy at or near the free surface of the source fluid to be ejected. To this end, it is desirable to control the free surface of a source liquid during droplet ejection because otherwise droplet ejection can be less accurate, and even fail.

Various methods and structures have been developed to affect the free surface of a source liquid pool in acoustic printing/ejection. For example, U.S. Pat. Nos. 4,719,476; 4,719,480 and 5,142,307 disclose techniques for spatially stabilizing capillary surface waves in liquid ink printing and similar applications.

U.S. Pat. Nos. 5,216,451; 5,428,381 and 5,686,945 disclose capping structures having openings for use with ink printing applications. U.S. Pat. No. 5,028,937 discloses an acoustic ink printer comprising a pool of ink having a free surface in intimate contact with the inner face of a perforated membrane and U.S. Pat. No. 5,808,636 discloses a method for reduction of droplet misdirectionality in acoustic ink printing. The above mentioned patents however do not include the features and benefits of the present invention as will described further below. Accordingly, an improved apparatus and method useful in controlling the free surface of a source liquid in a source liquid container is desired.

SUMMARY OF THE INVENTION

The present invention includes devices and methods for controlling the free surface of a liquid in a liquid containment structure such as a well of a well plate. The devices of the present invention generally feature a capillary positioned in a well of a well plate. In operation, liquid in the well moves up the capillary due to capillary action and arrives at a certain height. The height arrived at remains constant despite the source liquid depleting from the well.

In one embodiment of the present invention, a well plate includes at least one well, each well having a reservoir and a capillary lumen in fluid communication with the reservoir such that when a liquid is contained in the well, the liquid migrates at least part way up the capillary lumen. Preferably, the capillary lumen is integrally formed in a corner of each well. The capillary lumen can be cylindrical and have an inner diameter ranging from 0.1 to 4.0 mm. The capillary lumen may also be non-cylindrical and have, for example, a square or other shaped cross section. The capillary lumen may have a height equal to or greater than the height of the well or it may have a height less than the height of the well such that when a cover is attached atop the well plate, a gap is formed between the capillary lumen and the cover. The gap preferably ranges from 0.1 to 10 mm. The capillary lumen may also have an enlarged lower end section that varies in diameter. The enlarged lower end section may linearly or otherwise vary in diameter and have a maximum diameter at its lower tip. It is preferred that the capillary be upright but the capillary need not be upright. For example, the capillary may be positioned at an angle.

In a variation of the present invention, an insert for use with a well plate having a plurality of wells comprises a substrate having a plurality of ejection apertures. The insert further includes a capillary tube extending from each of the ejection apertures such that when the insert is positioned atop the well plate each capillary tube makes fluid communication with a liquid contained in the wells and the liquid moves at least part way up each capillary tube. The insert can further comprise a plurality of filling apertures and a lip surrounding the substrate such that the lip holds the substrate fixed atop the well plate.

In another variation of the present invention, an insert for use with a well plate having a plurality of wells comprises a frame and at least one capillary tube coupled to the frame such that when the insert is placed on top of the well plate the at least one capillary tube extends into a well of the well plate and wherein when a liquid is contained in the well, the capillary tube is in fluid communication with the liquid such that the liquid moves up the capillary tube. Preferably the frame comprises a plurality of struts and can have a lip around the frame for securing the apparatus atop the well plate. Other aspects of the capillary tube may be similar to the capillary tubes described in other variations of the present invention.

In another variation of the present invention an insert for use with a well plate having at least one well comprises a capillary and at least one support attached to the capillary such that when the capillary is positioned in the at least one well and when a source fluid is contained within the at least one well, the capillary is in fluid communication with the source fluid such that the fluid moves at least part way up the capillary. The insert can include 2–5 and more preferably 2–3 supports. The supports may be planar, curved or otherwise shaped. The insert may be integrally formed and be made of a variety of materials including various polymers and copolymers. The insert can be sized to fit within a well of a conventional well plate such as a 48-, 96-, 384-, 1536- and 3456-well plate or any "non-conventional" well plate containing any number of wells. The insert may also be sized to fit in a square-shaped well having a side length from 0.5 to 20.0 mm. The capillary may have various inner coatings or treatments such as a hydrophilic coating. Other aspects of the capillary tube may be similar to the capillary tubes described in other variations of the present invention.

In another variation of the present invention, an insert for use with a well plate comprises a tube having a base and a liquid restricting inlet in the base. The insert further includes at least one support attached to the tube such that the tube is positioned in at least one well and wherein when a source fluid is contained within the well, the tube is in fluid communication with the source fluid such that the source fluid forms a free surface at the restricting inlet and wherein the fluid does not migrate up the tube. The liquid restricting inlet preferably has an effective diameter of 0.1 to 4.0 mm and when the inlet is circular, it has a diameter of 0.1 to 4.0 mm. The insert may further comprise at least one spacer disposed at the base of the capillary tube such that when the capillary tube is positioned in the well, the inlet is spaced apart from the base.

In another variation of the present invention, an insert for use with a well plate having a plurality of wells comprises a substrate having a plurality of liquid ejection apertures. The insert further comprises a capillary tube extending from each capillary aperture such that when the insert is positioned atop the well plate each capillary tube makes fluid communication with a liquid contained in the well and wherein the liquid forms a free surface at a fluid restricting inlet of the capillary tube. The insert may also comprise a plurality of filling holes and a lip around the substrate such that the lip holds the substrate fixed atop the well plate. Other aspects of the capillary tube may be similar to the capillary tubes described in other variations of the present invention.

In another variation of the present invention, an insert for use with a well plate having a plurality of wells comprises a frame sized to fit on top of the well plate. The insert further includes at least one capillary tube coupled to the frame such that when the insert is placed on top of the well plate the at least one capillary tube extends into the well and wherein when a liquid is contained in the well, the capillary tube is in fluid communication with the liquid such that the liquid will form a free surface at a fluid restricting inlet of the capillary tube. Other aspects of the insert may be similar to the inserts described in other variations of the present invention.

In another variation of the present invention, a method for controlling an X-Y position of a maxima/minima point of a liquid meniscus comprises providing a well plate having at least one well, each well having a base region and a shelf region wherein the shelf region has a diameter larger than the base region and wherein when the liquid is introduced into the well, the X-Y position of the maxima/minima point remains constant as the liquid is depleted from the well. The base region may have an inner diameter ranging from 0.1 to 10.0 mm, 0.5 to 5.0 mm or 1.0 to 3.0 mm. The shelf may also have various coatings such as a hydrophilic or hydrophobic coating. The method may further comprise ejecting a portion of the liquid using acoustic energy.

In a variation of the present invention, a method comprises introducing a liquid into a base region to form a liquid level or meniscus within the base region. The liquid may be introduced such that the liquid level within the base region is greater or equal to the top of the base region by no more than half the effective diameter of the base region. Also, the liquid may be introduced into the base region such that the liquid level within the base region is less than or equal to the top of the base region by no more than half the effective diameter of the base region.

BRIEF DESCRIPTION OF THE DRAWINGS

The foregoing and other advantages of the invention will become apparent from the following detailed description and upon reference to the drawings in which:

FIG. 5C is a cross-sectional view of the well plate and inserts taken along line 5C—5C of FIG. 5B.

FIG. 11B also shows a well plate having a plurality of wells containing liquid.

FIG. 12 also illustrates the effects on a free surface of a liquid droplet as liquid depletes from the well.

Figure 1:
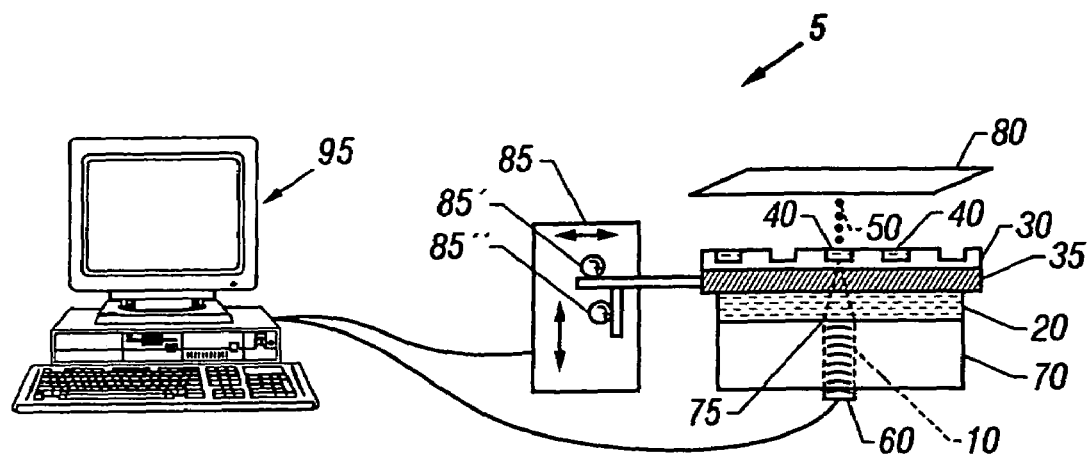
FIG. 1 is a schematic illustration of an acoustic liquid ejection system.

Although the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DETAILED DESCRIPTION OF THE INVENTION

The present invention includes devices and methods for controlling the free surface of a source liquid in a source liquid containment structure such as a well of well plate. The devices of the present invention preferably feature an upright capillary positioned in a well of a well plate. However, the capillary need not be upright. For example, the capillary may be positioned at an angle. In operation, source liquid in the well moves up the capillary due to capillary action and arrives at a certain height. The height arrived at remains constant despite the source liquid depleting from the well during the ejection process. Controlling the height or level of the source fluid in this manner has various aspects and advantages in liquid ejection systems as described hereinafter.

Non-Contact Liquid Ejection System

In order to understand the various aspects and advantages of the present invention, a liquid ejection system will first be briefly described. An example of a liquid ejection system is shown in FIG. 1. The figure depicts a non-contact fluid transfer apparatus 5 having at least one acoustic liquid deposition emitter 60 in electrical communication with a computer 95. During operation the acoustic liquid deposition emitter 60 generates an acoustic wave or beam 10 that can be propagated through an optional wave channel 70. The acoustic wave can be focused by a lens 75 prior to propagating through coupling fluid 20 to optimize the energy of the acoustic wave or beam 10 upon the liquid/air interface of source fluid 40. The acoustic wave 10 is propagated through a coupling medium 20 after which the wave is transmitted through source fluid containment structure 30 where the wave comes to focus at or near the surface of a pool of source fluid 40 thereby causing ejection of at least one droplet 50 of source fluid from the surface of the pool.

In one configuration, the ejected droplet 50 makes contact with a target 80. The source fluid containment structure 30 can be held on a movable stage 35. The movable stage 35 is controlled by actuator mechanism 85 which contains a horizontal actuator 85' or a vertical actuator 85" or a combination of the two actuators to control the movement of the stage 35 in both the vertical and horizontal directions. The actuator 85 is typically in communication with computer 95 which controls the movement of the stage to select a source fluid 40 or to adjust focusing of the acoustic wave or beam 10 upon the source fluid 40. The computer may have implemented thereon various algorithms to adjust the focal length and energy of the acoustic deposition emitter as well as control and manage the location of the acoustic deposition emitter relative to a particular source fluid present in or on a source fluid containment structure. An example of an acoustic liquid ejection system useful with the present invention is disclosed in U.S. patent application Ser. No. 09/735,709, entitled "Acoustically Mediated Fluid Transfer Methods And Uses Thereof", filed Dec. 12, 2000, now U.S. Pat. No. 6,596,239, and is hereby incorporated by reference in its entirety.

The above described ejection system as well as other liquid transfer systems can benefit from having predictable levels of source liquids in the source containment structures (e.g., the wells). Varying and unpredictable liquid levels in the source wells requires more complicated equipment and controls because the acoustic energy should be refocused at a new location which depends on the height of the free surface of the source liquid. If the acoustic energy is not properly focussed, inaccurate or no droplet ejection can result. Repositioning the acoustic energy emitter or otherwise compensating for the varying liquid free surface is not trivial and is preferably avoided.

Providing a stable free surface is another desirable goal in liquid ejection systems. In particular, the ejection of droplets causes waves and "sloshing" formed in the source fluid. The waves or "sloshing" distorts the free surface and can misdirect liquid droplets as they are ejected from the free surface at an undesirable angle.

Accordingly, the present invention provides various structures and methods to control the free surface of liquid in a source liquid containment structure such as a well of a multi-well plate.

Well Having Capillary Lumen

Figure 2A:
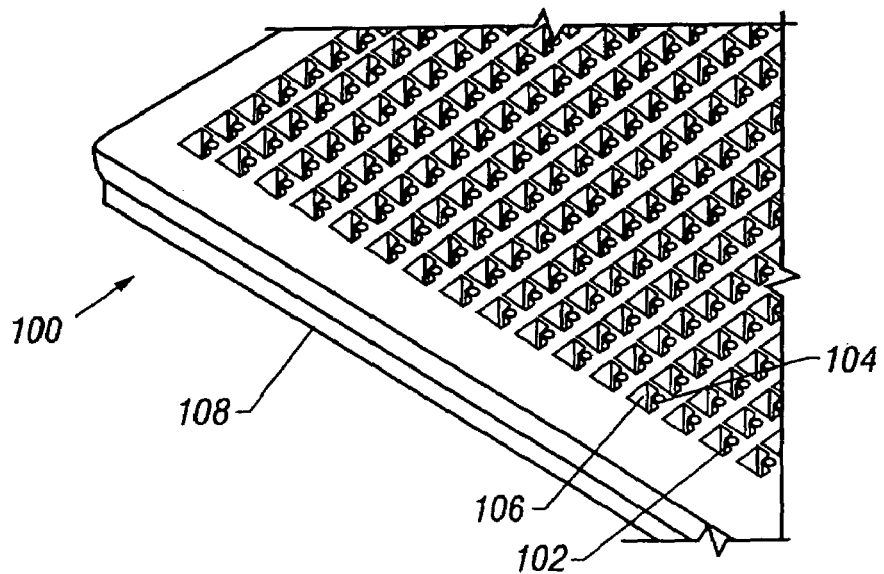
FIG. 2A is a partial perspective view of a well plate assembly in accordance with the present invention.

FIG. 2A illustrates an exemplary well plate 100 in accordance with the present invention. By well plate it is meant a sample holding device that includes one or more wells which can be used in, for example, combinatorial chemistry and high throughput screenings.

As shown in FIG. 2A, well plate 100 includes many wells 102 for containing a source liquid. Each well features a capillary lumen or tube 104 disposed upright in the corner of the well. Liquid can be inserted into the well through opening 106 of the well and the liquid will be drawn up the capillary lumen by capillary forces.

The height that the liquid achieves in the capillary lumen is repeatable and does not vary with the amount of liquid in the well given there remains some liquid in the well. We attribute this phenomena to capillary forces predominating the system. Additionally, the free surface of the liquid within the small diameter tube 104 has less "sloshing" when liquid droplets are acoustically ejected from the free surface (discussed further below) and when the device is moved. We attribute the stable free surface to various forces acting on the liquid including surface tension, adhesion forces between the fluid and the wall of the capillary and cohesion forces between the like molecules of the fluid. The balance of these forces are estimated by the following equation: $h=(2 \times \gamma \times \cos\theta)/(\rho \times r \times g)$ where h is the height at which the fluid will rise in the capillary of radius r; θ is the contact angle of the fluid in the tube, γ is the coefficient of surface tension, g is the acceleration due to gravity and ρ is the specific gravity of the fluid. Thus, if the diameter of the capillary tube is chosen properly, liquid can be drawn to a predictable position such as the top of the capillary lumen.

Figure 2B:
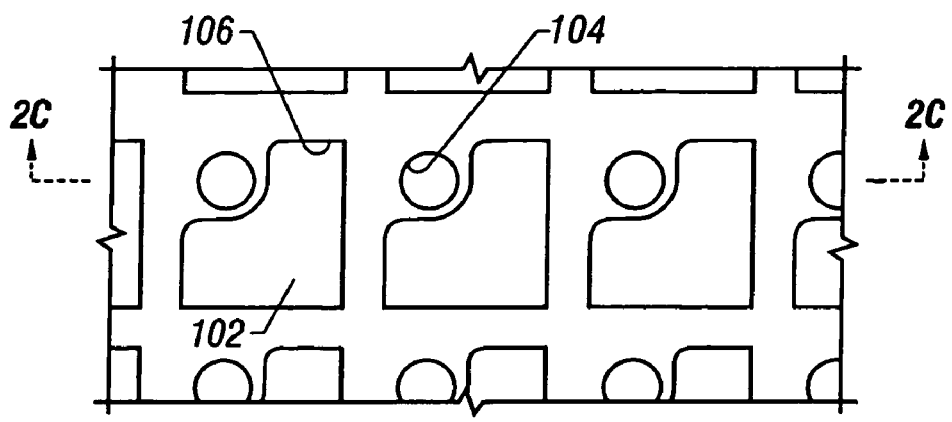
FIG. 2B is a partial top view of the well plate assembly shown in FIG. 2A.
Figure 2C:
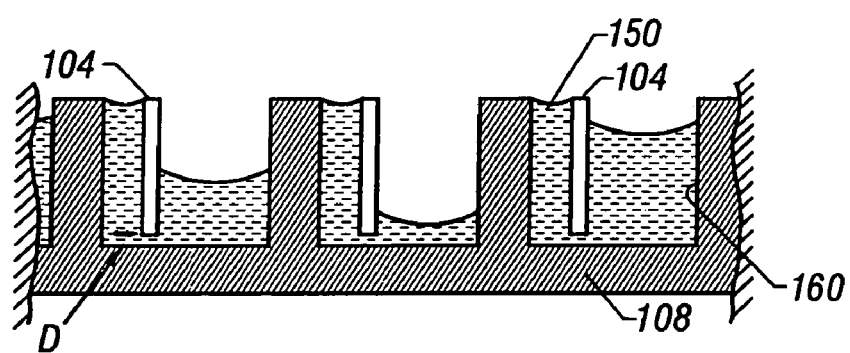
FIG. 2C is a cross-sectional view of the well plate assembly shown in FIG. 2B taken along line 2C—2C.

FIGS. 2B and 2C show the well plate embodied in FIG. 2A in greater detail. FIG. 2B is a partial top view of the well plate 100 and FIG. 2C is a cross section taken along line 2C—2C of FIG. 2B. As shown, capillary lumen 104 is upright and is located in a corner of well 102. The capillary lumen 104 is useful when transferring liquids from the well of the well plate. When an acoustic non-contact fluid transfer method is used to transfer fluid from the well, the acoustic energy may be focussed near or at the free surface or meniscus 150 in capillary 104, thus ejecting a droplet normal to the plane of the meniscus 150. Because of capillary action, even as the fluid level of the large reservoirs 160 decreases, the height of the fluid in the capillary remains the same. Furthermore, the surface of the meniscus 150 remains stable; i.e., waves are quickly dampened and "sloshing" is minimized. Use of the capillary lumen in accordance with the present invention thus allows droplets to be ejected more accurately and at an intended trajectory.

The present invention is compatible with a wide variety of fluids or solutions. As stated above, the height to which a given solution will rise in the capillary tube will depend upon at least the geometry of the capillary and the endogenous properties of the solution. The dimensions of the capillary can be selected based upon the nature of the solutions to be used. The radius (or diameter) of the capillary lumen, and the height can be easily altered to adjust the height at which a solution (or class of solutions) will reach in the capillary. Typically a radius will be chosen so that the fluid will be drawn to the top of the capillary or insert. The inner diameter of the capillary lumen can range from 0.1 to 4.0 mm and more preferably from 0.5 to 3.0 mm. The inner diameter or effective inner diameter of the well is required to be greater than that of the capillary. A suitable diameter or side length for the well ranges from 0.2 to 20 mm and more preferably from 2 to 10 mm. Alternatively, the ratio of the effective surface area of the capillary to the well ranges from 0.01 to 0.5 and more preferably from 0.02 to 0.2.

In the well plate of the present invention, the number of wells can be varied from a single well to a more densely packed array of many hundreds of wells. A suitable number of wells is 384.

The shape of the wells may also vary. FIGS. 1–7 show square wells, but these fluid-containing wells could be round, rectangular, or otherwise shaped. Almost any well size that can accommodate a capillary is possible. This invention works particularly well with large wells or fluid sources. One of the advantages of the capillary is that it can reduce many of the surface waves and irregularities that arise with fluid wells of large cross-sectional area which can be particularly problematic to non-contact fluid transfer methods. Surface waves are more quickly dampened in the confined area of the capillary. The overall plate size and shape could also vary from the rectangular plate which matches the average dimensions of many commercially available multi-well plates. Larger and smaller dimensions are also contemplated.

The well plates may be fabricated as a single piece, including the wells and the capillary lumen or tubes. The well plates could be fabricated from any appropriate material that provides substantial structural integrity. However, polymeric and-copolymeric materials such as polycarbonate, polytetrafluoroethylene, polypropylene, polystyrene, or cyclo-olefin copolymers are preferred.

The present invention could also be fabricated separately and assembled. The parts could be made of different materials. For example, it is contemplated that the bottom of the well 108 could be a made of a material such as silicas (or other appropriate material) while the sides of the chamber are made of a polymeric plastic. Such embodiments could be useful for the non-contact method of fluid transfer, where it would be desirable to have the bottom of the well plate 108 be made of a material of a specific acoustic impedance. Preferably, the capillary lumen and side walls of the wells are molded as one component and a plastic film is joined to the bottom to form the reservoirs. The film is preferably thin and has a minimum acoustic impedance. A suitable thickness for the thin film is from 1 micron to 1.0 mm and more preferably from 1 to 100 microns. Suitable materials for the thin film include polymeric materials such as polypropylene however other materials may be used.

The present invention could also be fabricated by modifying conventional well plates. For example, a conventional well plate may be machined to fit a capillary tube in each well. First, the top and or bottom of the well plate (e.g., a Greiner™ 384-well plate) are cut off. Next a slot or throughhole is created in each well to fit a capillary tube. For example, a cylindrical slot may be drilled from the bottom of the well plate. The cylindrical slot may extend partially or completely through the well plate. The slot or through-hole should have an inner diameter large enough to accommodate a capillary tube. An exemplary capillary tube has an outer diameter of 2.95 mm and a length of 5.85 mm. However, other dimensions may be suitable.

After the slots are created in each of the wells, a suitably-sized capillary tube is inserted into each slot. The capillary tube preferably forms a press fit with the slot but may be further secured with an adhesive such as epoxy. A thin film is then bonded (e.g., thermally bonded) to the bottom of the well plate forming a base in each of the wells. A suitable thin film is a 0.1 mm thick sheet of polypropylene. The thin film seals the bottom of each well to create a containment structure for various liquids. Liquid introduced into the well will contact the bottom of the capillary tube and migrate up the capillary tube to a given height.

This invention also contemplates coating the capillary lumen or tubes to alter the adhesive properties of the fluid to the sides of the capillary. Adhesion of the fluid to the material of the capillary depends upon both the surface of the capillary and the fluid. Thus surface properties of the interior of the capillary such as charge (or polarity) could be modulated by coating a charged or polar/nonpolar (i.e. hydrophilic/hydrophobic) substance within the capillary. For example, a hydrophilic coating on the interior of the capillary is suitable for most biological fluids. Nonlimiting examples of suitable hydrophilic coatings include substances that contain amino, hydroxyl, and carboxyl groups. Plasma and corona surface treatments may also be utilized to change the surface properties of the capillary. For instance, a plasma treatment may be applied to increase the wettability of the capillary.

The shape of the capillary may also vary. As shown in FIGS. 2–3, the capillary lumen has a substantially circular cross-sectional area. The invention is not so limited. Lumens of different cross-sectional area (e.g. square or oval) could be used. Such alternate shapes might be appropriate for wells of different dimensions. Furthermore, FIGS. 1–3 show capillary tubes which are open at the bottom and separated from the bottom of the well by a very small distance D. However, an alternative embodiment could have the capillary lumen connected to the bottom of the well plate and have an opening on one side of the tube near the bottom to allow fluid entry.

In the embodiments shown in FIGS. 2–3, the separation distance between the bottom of the capillary lumen and the bottom of the well is not great, but must be adequate to allow solution to flow from the body of the well into the capillary lumen. If the distance separating the capillary lumen from the bottom of the well is too small, the rate at which the capillary "refills" after transferring fluid may be limiting when fluid is being transferred at a rapid rate. A suitable distance D is from 0.05 to 5 mm and more preferably from 0.1 to 1.0 mm.

Figure 3A:
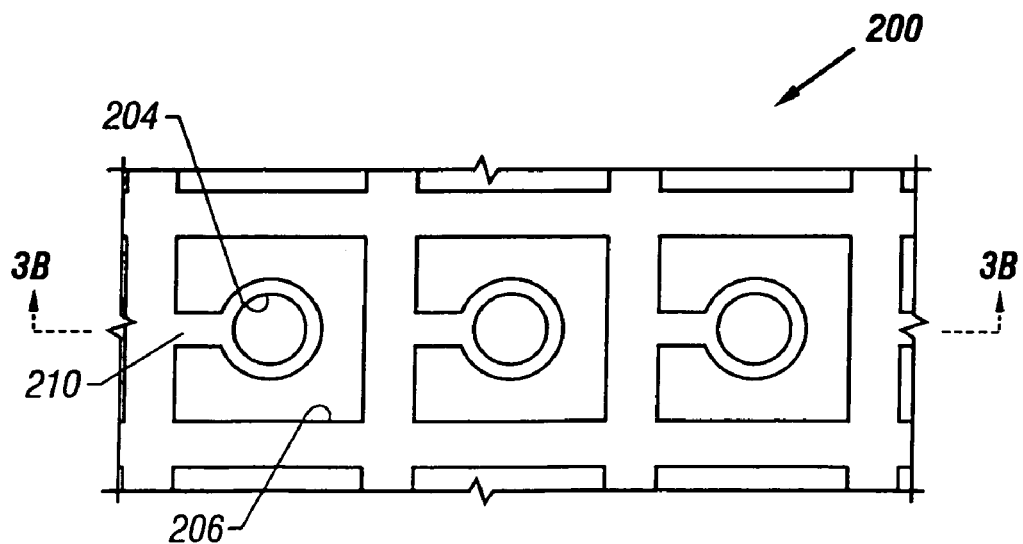
FIG. 3A is a partial top view of another embodiment of a well plate assembly in accordance with the present invention.
Figure 3B:
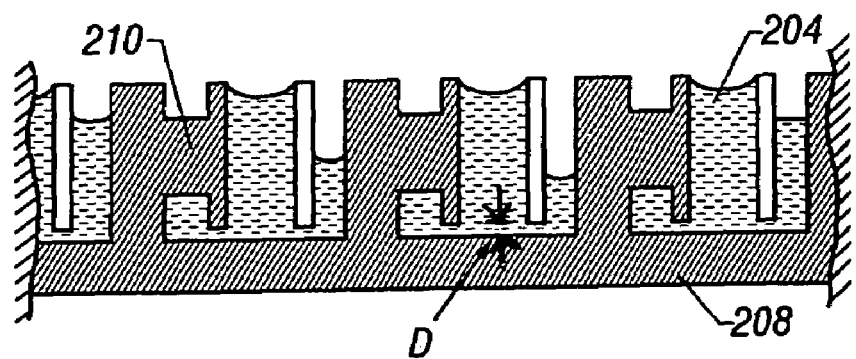
FIG. 3B is a cross-sectional view of the well plate assembly shown in FIG. 3A taken along line 3B—3B.

The capillary is located in the corner of each well of the well plate in FIGS. 2A and 2B. However, the capillary lumen may be placed at alternate positions in the well. For example, FIGS. 3A and 3B show a capillary tube 204 located in the center of wells 206. The capillary tube 204 is connected to the side of the well by an arm 210.

Figure 4A:
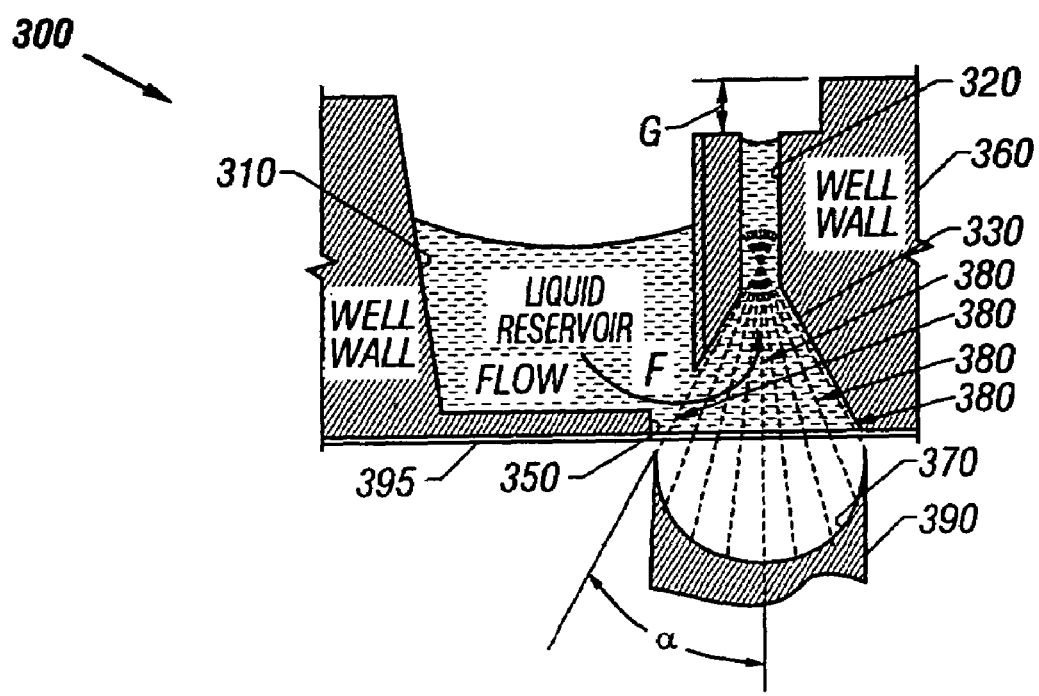
FIG. 4A is a partial cross sectional view of a well having a capillary lumen with an enlarged end section in accordance with the present invention.
Figure 4B:
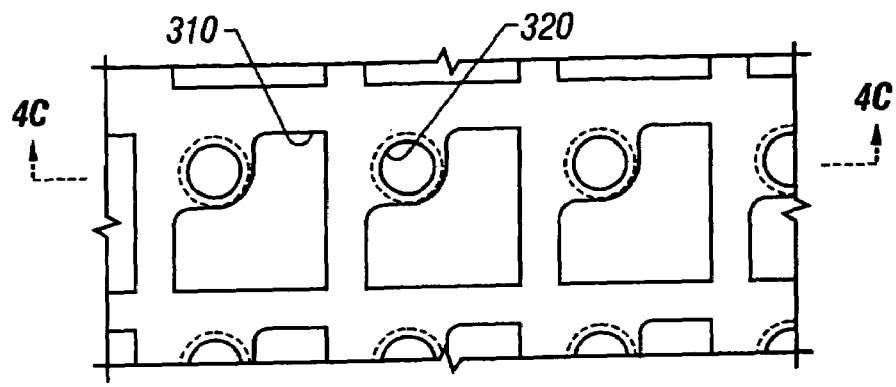
FIG. 4B is a partial top view of a well plate having a number of the wells, each being similar to the well depicted in FIG. 4A.
Figure 4C:
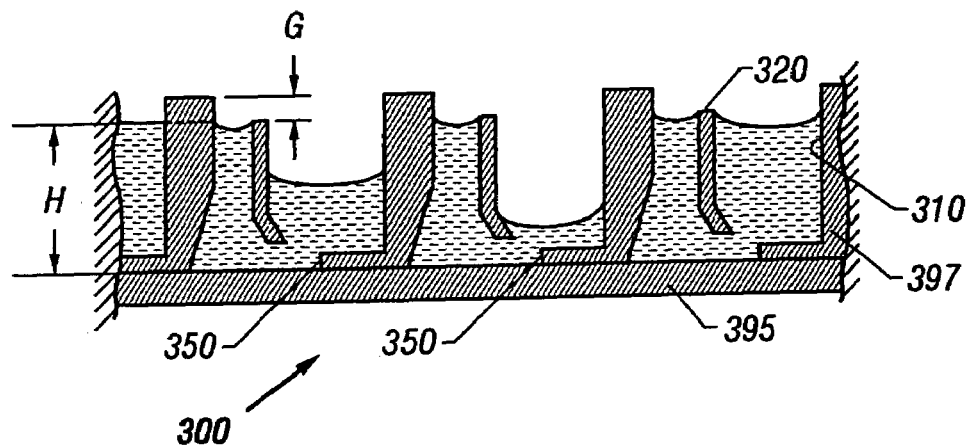
FIG. 4C is a cross-sectional view of the well plate taken along line 4C—4C of FIG. 4B.

FIGS. 4A to 4C illustrate another exemplary configuration of the well plate of the present invention. Referring to FIG. 4A, a cross section of a well 300 containing liquid is shown. The well 300 comprises a reservoir 310 and a capillary lumen 320 in fluid communication with the reservoir 310. The capillary lumen 320 shown in this embodiment has a height less than that of the well.

A suitable capillary height is from 1 to 10 mm and more preferably from 3 to 6 mm. However, the height of the capillary may vary. The following equation may be used to select a capillary lumen length ($L_{CL}$):

$$L_{CL} = D_W - C - G$$

where $D_W$ is the depth of the well and C is the clearance between the bottom of the well and the bottom of the capillary lumen and G is the gap from a top surface of the well plate to the top of the capillary lumen. In this embodiment, the length of the capillary lumen preferably varies with the depth of the well, but the clearance and the gap could remain relatively constant regardless of the depth.

When a cover or lid is placed atop the well a gap (G) is created. Gap G is advantageous in certain applications and in particular, when a cover is heat sealed to the well plate to enclose the liquids or samples contained in the wells. The gap prevents heat generated during the sealing process from damaging or denaturing samples in the wells. The gap (which is typically air) thus acts as a heat insulator.

Another embodiment of the present invention (not shown) includes a capillary lumen having a height equal to or greater than the height of the well.

Capillary lumen 320 also features an enlarged lower end section 330. The lower end section increases in diameter at an angle ($\alpha$) which can range from 1 to 70 degrees and more preferably from 5 to 50 degrees and most preferably 10 to 30 degrees. The enlarged end section thus has a maximum diameter at a lower tip closest to the well base. The inner diameter at this tip ranges from 0.1 to 4.0 mm and is preferable between 0.5 and 3.0 mm. The enlarged end section 330, however, must not be so large that liquid is prevented from migrating up the capillary 320 from capillary action alone. The enlarged lower end section may vary in diameter linearly and have a constant angle of expansion. The enlarged lower end section may also be nonlinearly shaped. Thus, the lower section may be curved in some embodiments.

The flared or enlarged end section of capillary 320 is particularly well suited for acoustic ejection systems because acoustic energy is collected more efficiently from a lens 390 positioned below the well. Energy from the entire lens surface 370 can thus be transmitted directly into the liquid within the capillary. The enlarged end section 330 may preferably be shaped according to a ray trace 380 of the lens 390.

The structure depicted in FIGS. 4A to 4C also includes a through-hole 350. Through-hole 350 is a feature that facilitates manufacturing of the well plate 300. In particular, the presence of through-hole 350 simplifies the mold tooling for injection molding. This configuration provides for the top portion of well plate 300 to be conveniently injection molded and the bottom 395 formed separately. Preferably, the bottom part 395 is a thin film bonded to the injected molded upper half 397. Attaching the film 395 to the molded upper part containing the capillary and well structures can be carried out in a variety of ways including heat bonding, adhesives, ultrasonic welding, etc.

FIG. 4C also illustrates the consistent liquid height (H) in the capillary lumen despite the varied amounts of liquid in the larger reservoirs. The liquid will typically flow or travel up to the top of the capillary lumen so long as there are not regions in the reservoir having a stronger capillarity and there is sufficient amount of liquid in the well.

Figure 5A:
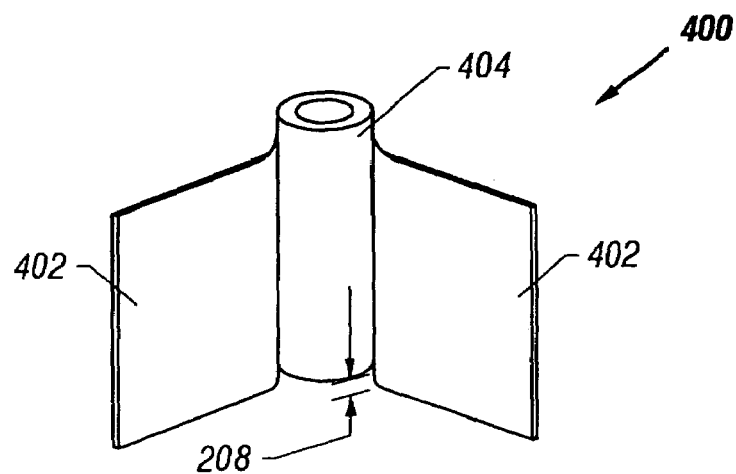
FIG. 5A is a perspective view of an insert in accordance with the present invention.

In another variation of the present invention, the capillary lumen may be a separate component (e.g., an "insert") mounted or positioned in the well of a well plate. FIG. 5A is an example of an insert 400 that can be deployed in a fluid source containment structure such as a well plate. The insert 400 includes a capillary tube 404, and at least one support. In FIG. 5A supports are two wing-like tabs 402 which project from the outer surface of the capillary tube to hold the tube in an upright position. The support tabs 402 also maintain the separation distance 208 between the bottom of the capillary tube and the bottom of the fluid source (well) in which it sits.

Figure 5B:
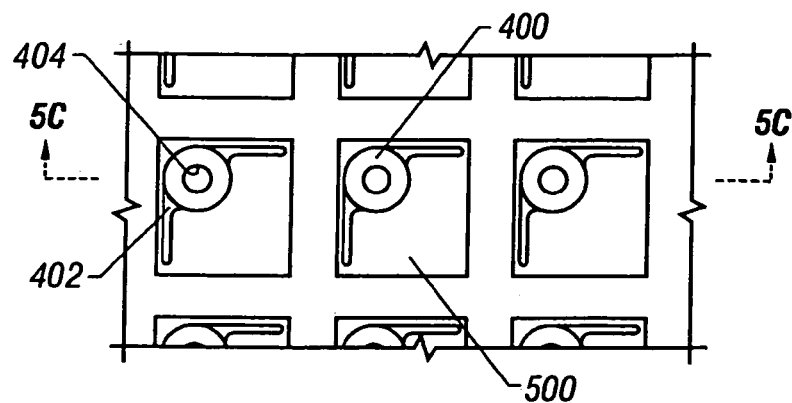
FIG. 5B is a partial top view of a well plate having a number of inserts positioned in individual wells in accordance with the present invention.

The location and shape of the support tabs 402 can vary widely. In the embodiment pictured in FIG. 5A, two support tabs are separated by 90°. This embodiment conforms with square fluid source wells, as shown in FIG. 5B. However, the support tabs may be otherwise configured, including but not limited to a circular support tab for wells that have a round cross-sectional area, or tripod-like support tabs separated by 120°. A suitable number of supports is 2–5 and more preferably 2–3.

The inserts shown can be used with many commercially available multi-well plates. These plates come in a variety of well sizes, shapes and volumes: multi-well plates with 1, 4, 6, 12, 24, 48, 96 and 384 wells are all readily available. The inserts can be designed to adapt to these commercially available plates, by adjusting the shape, size and number of the support tabs and the capillary size. For example, the diameter of a well in a 96 well plate may be about 0.7 cm and hold a sample volume upwards of 400 ul. The diameter of a well in a typical 384 well plate may be about 0.350 cm and hold a sample volume upwards of 100 ul. An exemplary depth may be around 1 cm and upwards.

FIG. 5C shows a cross-sectional view of the insert shown in FIG. 5B taken along the line D—D. The insert 400 fits completely into the fluid source well 500 of the multi-well plate. As the fluid in the well is transferred and depleted 502, the supply of fluid at the site 504 of fluid transfer is kept steady and at a constant height by the insert 400.

Figure 6A:
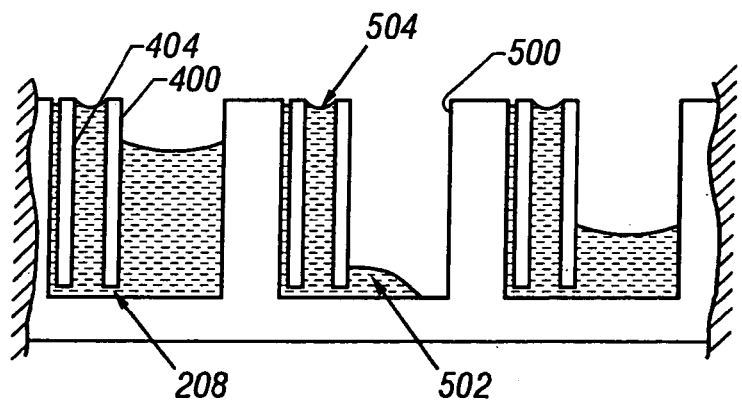
FIG. 6A is a partial perspective view of an insert atop a well plate wherein the insert includes a number of capillary tubes in an array or grid and coupled together via supports.
Figure 6A:
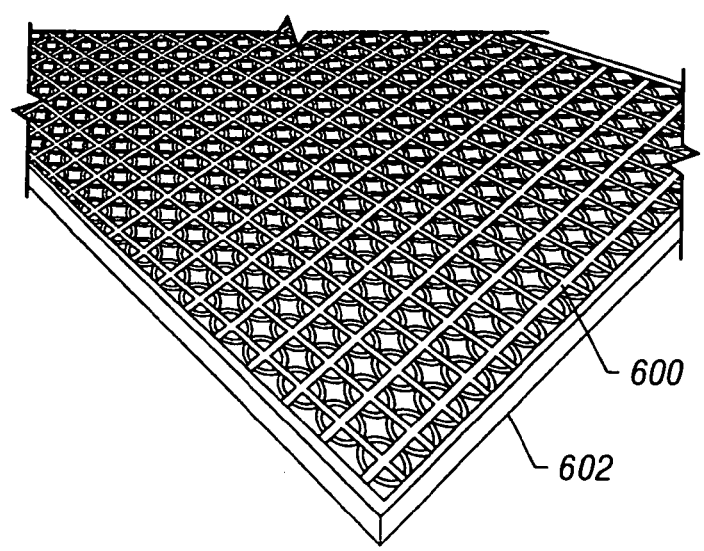
Figure 6B:
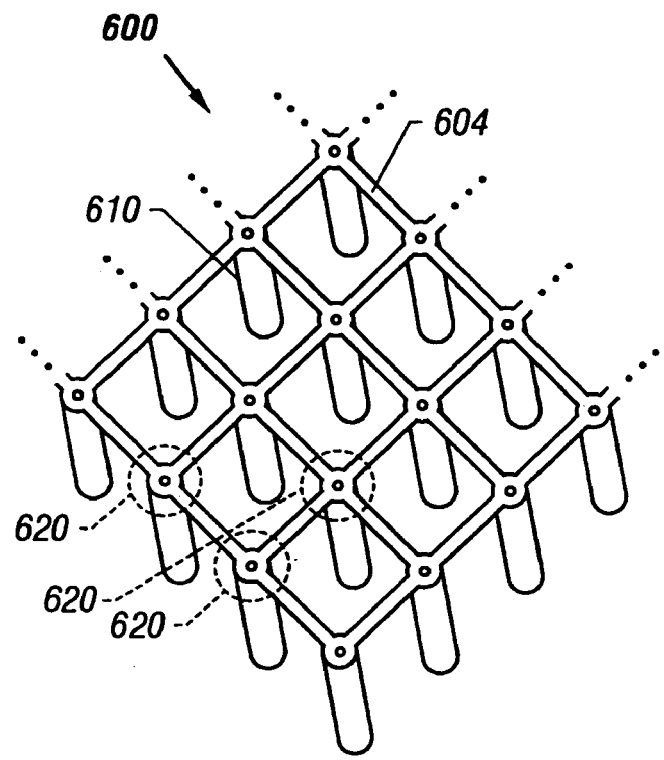
FIG. 6B is a partial perspective view of the insert shown in FIG. 6A.

FIGS. 6A and 6B show another embodiment of an insert 600. The insert 600 shown in FIGS. 6A and 6B features an array of capillary tubes 610 linked by an insert frame 604 that keeps them in a spaced configuration. FIG. 6A shows the insert with multiple capillary tubes inserted into a multi-well plate 602. The insert frame is a grid of struts 604 that hold the capillary tubes together at the vertices 620 of the grid. Each capillary tube of the insert is positioned to fit into each well of a multi-well plate and the insert frame sits on the top of the multi-well plate holding the capillary tubes slightly above the bottom of the plate, allowing fluid access to the interior of the capillary tube through the open bottom of the tube. When there is fluid present in the tube, the fluid is drawn up into the capillary tube by capillary action. Depending on the liquid and the dimension of the capillary, liquid will be drawn to a repeatable and predictable level in the capillary tube.

FIG. 6B shows a higher magnification of the grid of struts and attached capillary tubes. As shown, the insert 600 can be fabricated as a single, integrated piece, using a technique like injection molding. The insert can be made of any appropriate material that provides substantial structural integrity; polymeric materials such as polycarbonate, polytetrafluoroethylene, polypropylene or polystyrene could be used, which have the added advantage of being biocompatible. The capillary tubes may also be detachably connected to the frame 600. For example, the frame and tubes may have interlocking tabs which snap into position when pushed together.

As with the individual inserts, an array of inserts like those shown in the embodiments of FIGS. 6A and 6B can be made to conform to commercially available well plates. Commercially available plates with 4, 6, 12, 24, 48, 96 and 384 wells are examples, but the invention is not limited to these. The spacing of the capillary tubes, as well as the height of the capillary tubes can be adjusted to fit different well plates and fluid source containers. Also, the inserts can be designed with proper dimensions so that an interference fit is formed when the insert and well plate are combined. In this case, the insert is detachably connected to the well plate.

Figure 7A:
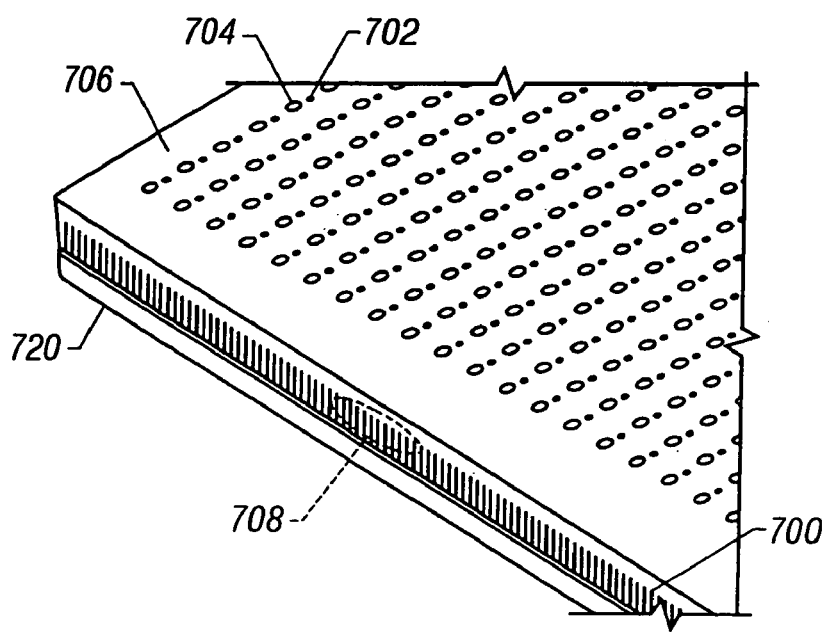
FIG. 7A is a partial perspective view of another embodiment of the present invention including a cover positioned atop a well plate.
Figure 7B:
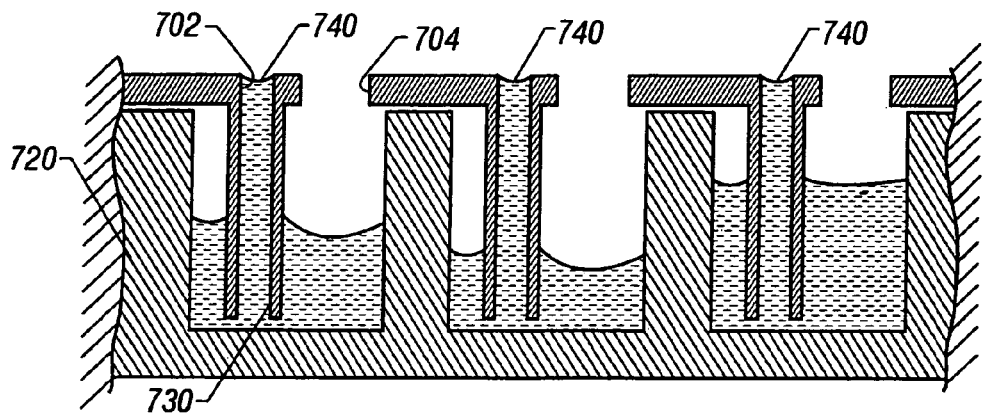
FIG. 7B is a partial cross-sectional view of the cover and well plate shown in FIG. 7A.
Figure 8A:
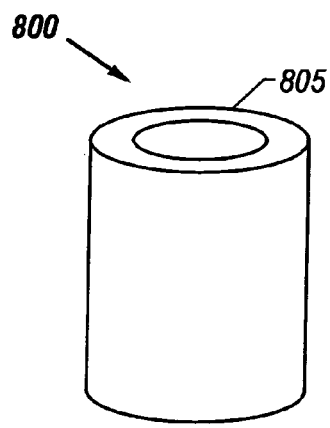
FIGS. 8A–8D are perspective, top, front, and bottom views respectively of an insert having a restricting inlet in accordance with the present invention.
Figure 8B:
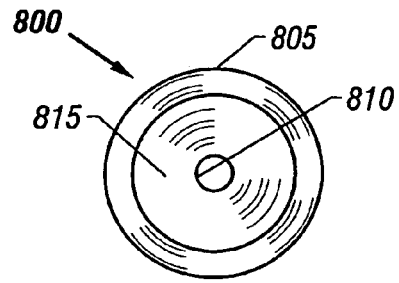
Figure 8C:
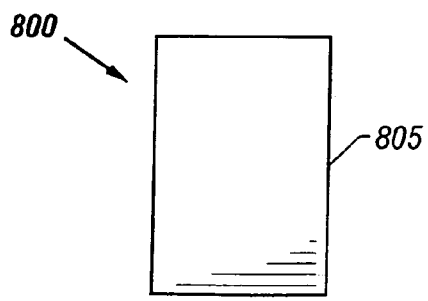
Figure 8D:
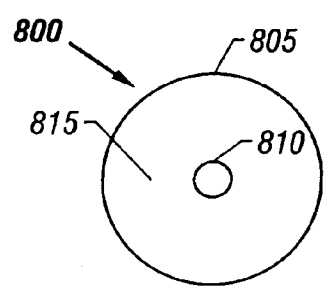

FIGS. 7A and 7B show another embodiment of the present invention having multiple capillary tubes. In this embodiment, an apparatus includes a cover or substrate 706 that fits like a lid atop a well plate 720. The substrate 706 comprises a plurality of sample ejecting apertures 704 for ejecting droplets of liquid. Extending downward from the sample ejecting apertures are capillary tubes 730. The capillary tubes 730 are designed and function similar to the capillary tubes described above. Thus liquid droplet ejection is improved because the free surface 740 is maintained at a predictable level with minimal waves or sloshing.

The apparatus shown in FIGS. 6–7 can also include a lip or edge 700 to hold the insert in position on the well plate. This lip could also be textured 708 to facilitate handling. This embodiment protects the wells of the well plate because except for the sample filling apertures 704 and the sample ejection apertures 702, each well is covered by the substrate 706.

Tubular Insert Having Fluid Restricting Inlet

FIGS. 8–11 show another variation of the present invention. In particular, an insert 800 is provided which controls the free surface of a source liquid in a well of a multi-well plate. FIGS. 8A–8D respectively show perspective, top, side, and bottom views of the insert 800. The insert 800 shown in these figures comprises a cylindrical tube 805 and a fluid restricting inlet 810 in a base region 815. The restricting inlet 810 has a diameter less than the diameter of the tube 805. The inlet 810 is a small aperture formed in base 815 and is a region of high capillarity. A suitable inner diameter for the high capillarity restricting inlet 810 is from 0.1 to 4.0 mm and more preferably from 0.5 to 2 mm. A suitable inner diameter for the tubular member 805 is from 0.2 to 10 mm and more preferably from 1.5 to 5 mm.

Figure 9:
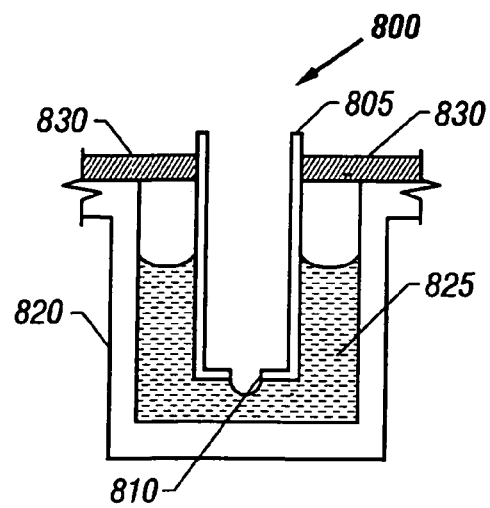
FIG. 9 is a cross section of the insert shown in FIGS. 8A–8D positioned in a well of a well plate wherein the insert is held in place with support members.

FIG. 9 depicts a cross section of a well 820 of a multi-well plate having an insert 800 disposed therein. Notably, liquid 825 in the well 820 forms a meniscus at fluid restricting inlet 810. The meniscus or free surface forms at the inlet 810 regardless of the level of the source liquid in the well. In this manner, the inlet acts as a fluid stop. The free surface of the liquid is thus held at a predictable level for droplet ejection or withdrawal in liquid transfer applications. We attribute this phenomena to the high capillarity of the inlet 810.

FIG. 9 also depicts supports or frame members 830 holding tube 800 in place. Frame members 830 are attached to insert 800 and sit on (or are fastened to) well 820 such that the free surface formed at the high capillary inlet 810 is positioned a suitable distance from the base of the well. The separation distance ordinarily ranges from 0.050 to 10 mm and more preferably from 0.2 to 4.0 mm.

Figure 10A:
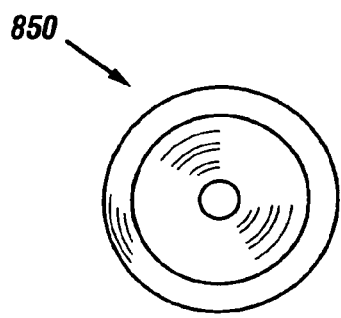
FIGS. 10A–10C are top, front, and bottom views of another insert in accordance with the present invention; the insert shown in FIGS. 10A–10C includes spacers.
Figure 10B:
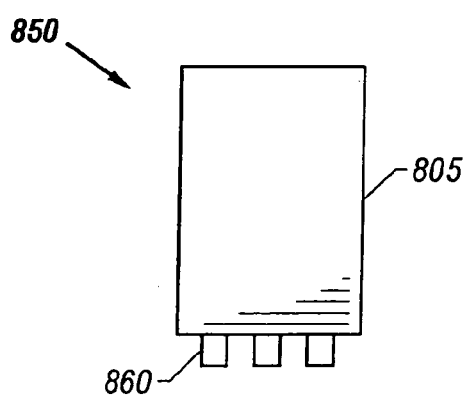
Figure 10C:
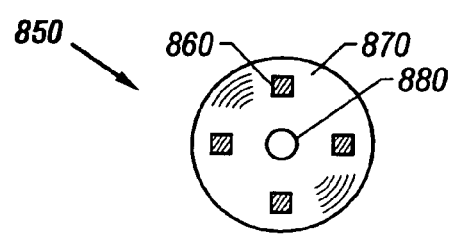

Alternatively, as depicted in FIGS. 10A to 10C, an insert 850 may comprise at least one spacer 860 extending from a base region 870. The spacers 860 contact the base of the well (not shown) and hold the inlet 880 a predetermined height above the base of the well. This separation distance is desirably equal to the separation distance discussed above with respect to FIG. 9. The spacers are shown having square cross sections but need not be so limited. The shape of the spacers may vary. Preferably, the spacers occupy a volume so as not to disturb or hinder droplet ejection. The spacers also must be large enough to have structural rigidity. In one variation, the spacers may also extend radially to contact the side walls of a well. The spacers in this configuration may fit snugly such that further holding means is not required to keep the inserts in proper position.

Figure 11A:
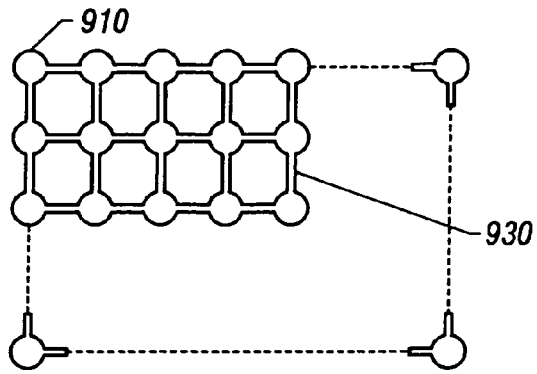
FIG. 11A is a partial top view illustrating a number of plastic inserts in an array or grid and coupled together via supports.
Figure 11B:
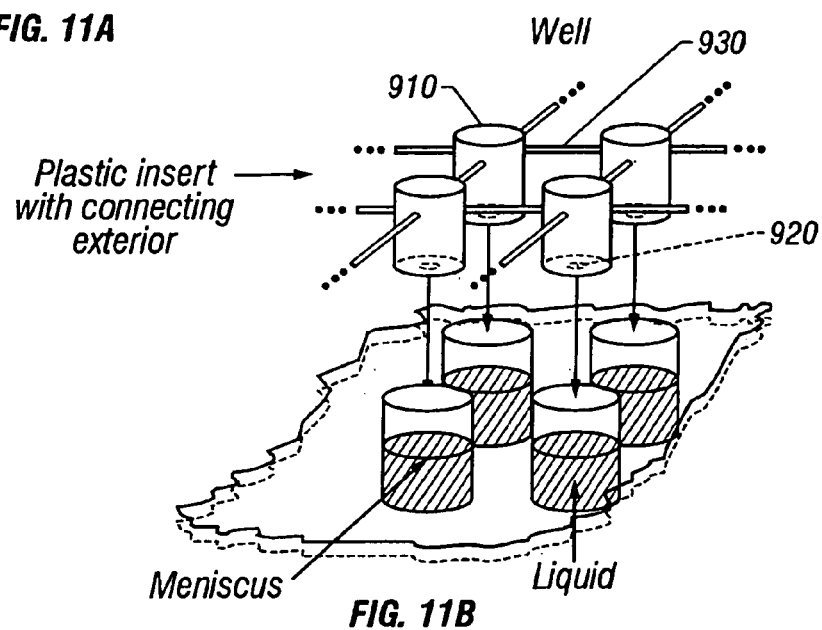
FIG. 11B is an exploded view of a plurality of inserts coupled together via supports.

FIGS. 11A and 11B depict another embodiment of the present invention including a plurality of inserts as disclosed in FIGS. 8–10 except that the inserts are joined in an array. FIG. 11A shows a top schematic view and FIG. 11B shows a partial exploded view. Each tube 910 includes a restricting inlet 920 as described above. The high capillarity or restricting inlet is sized such that a meniscus or free surface forms across the inlet 920 regardless of the volume of fluid in the well of the well plate. FIGS. 11A and 11B additionally show frame and strut members 930 to interlock and hold the tubes together. In this manner, an array of tubes may be joined (e.g., detachably) and registered/aligned with corresponding wells of a multi-well plate. The frame sits on top of the well plate thereby positions the inlets a fixed distance from the base of the wells.

Well Having Shelf Region

Figure 12:
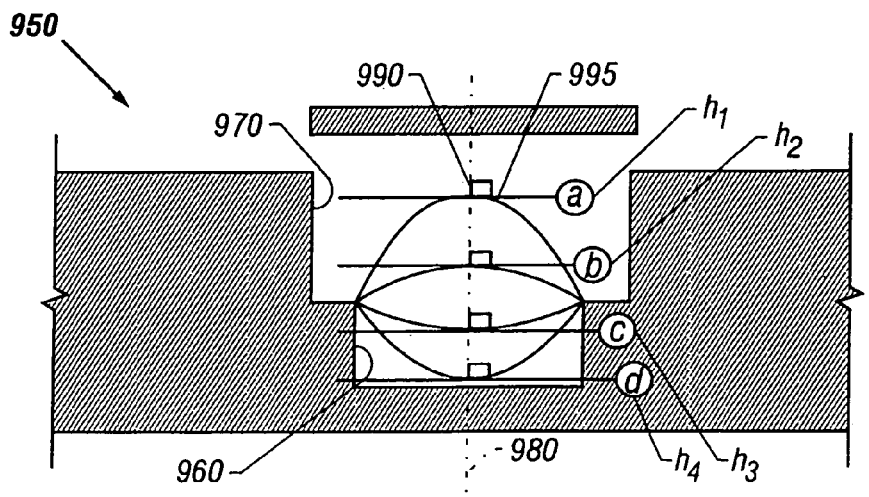
FIG. 12 shows a partial cross sectional view of another embodiment of the present invention including a well having a base region and a shelf region.

FIG. 12 shows a partial cross section of another embodiment of the present invention. This embodiment includes at least one well 950 having a base region 960 and a shelf region 970 wherein the shelf region has an effective diameter larger than the base region. For example, base region 960 can have an effective diameter from 10% to 99.9% of the shelf region. Suitable effective diameters for the base region range from 0.1 to 10.0 mm, 0.5 to 5.0 mm and more preferably 1.0 to 3.0 mm.

Liquid introduced into the well 950 is confined to the base region due to the higher capillarity of the base region as compared to the shelf region. Additionally, the shelf region 970 can include a hydrophobic coating to prevent certain liquids from migrating or adhering to the shelf region.

The shape of the well 950 may vary greatly. It may be cylindrical, cubic, or otherwise shaped. During operation, the free surface of liquid in the well falls as shown in FIG. 12 with reference to $h_1$, $h_2$, $h_3$ and $h_4$. However, the height of the contact points between the liquid and the well surface does not change; liquid does not slide down the side of the inner surface of the well. That is, as droplets are ejected and the liquid volume decreases, the shape of the meniscus or free surface changes lowering the liquid level but the height of the contact points between the liquid and inner well surface does not change.

Notably, the well structure of the present invention controls the X-Y position 980 of a maxima/minima 990 of the meniscus surface 995. This is because the X-Y position of the maxima/minima 990 of meniscus surface 995 is a function of the contact points between the liquid and the base surface. Since these points do not change as liquid is drained, the X-Y position 980 of the maxima/minima 990 of the meniscus remains unchanged. Controlling the X-Y location of the maxima/minima is useful in droplet ejection applications because the slope of the free surface at this location is zero. Consequently droplets can be ejected from this X-Y location in a predictable direction.

The base region could be very shallow or deep. So long as liquid is introduced in a sufficient amount such that the contact points between the liquid and the inner well surface do not change or slip down, the X-Y position of the maxima/minima may be maintained. Excess liquid should not be added to the base region such that the liquid moves into the shelf region. The amount of liquid that can sit above the well may be determined by the physical properties of the fluid; namely the surface tension and density. If the liquid has a very high surface tension and very low density, enough liquid may be introduced until a sphere is formed. However, if the fluid is either very dense or has a very low surface tension, only a slight convex meniscus may be created before the liquid breaches into the shelf region.

A preferred embodiment of the above mentioned method is that liquid may be introduced such that the liquid level within the base region is greater or equal to the top of the base region by no more than half the effective diameter of the base region. Likewise, the liquid may be introduced into the base region such that the liquid level within the base region is less than or equal to the top of the base region by no more than half the effective diameter of the base region.

Although the foregoing detailed description of various embodiments of the present invention is set forth in some detail, the invention is not limited to those details. A liquid volumetric or height control device or well plate made or used according to the invention may differ from the disclosed embodiments in various ways. In particular, it will be appreciated that embodiments of the present invention may be employed in many different applications for transferring fluid, not limited to non-contact transfer methods. Free surface or volumetric control devices according to the invention may have utility in affecting fluid transfer using needle-, pin- or contact-based methods, and other applications.

All publications, patent applications, patents, and other references mentioned in this application are incorporated by reference in their entirety. To the extent there is a conflict in a meaning of a term, or otherwise, the present application will control.

The invention claimed is:

1. A liquid dispensing apparatus comprising:
   a well plate comprised of one or more wells, each of the wells having a reservoir and a capillary lumen in fluid communication with the reservoir such that when a liquid is contained within the reservoir, the liquid migrates at least part way up the capillary lumen due to capillary forces; and
   an acoustic wave emitter positioned adjacent to the well plate, the acoustic wave emitter configured to emit acoustic energy that causes a portion of the liquid in the capillary lumen of at least one of the wells to be ejected from the capillary lumen.

2. The apparatus of claim 1 further comprising:
   a translational means for holding the well plate and for moving the well plate in a horizontal and/or vertical direction relative to the acoustic wave emitter.

3. The apparatus of claim 1 wherein said acoustic wave emitter is configured to propagate a focused acoustic beam through a bottom of the well plate, then through the liquid contained within the capillary, and toward a free surface of the liquid within the capillary lumen.

4. The apparatus of claim 3 wherein the focused acoustic beam is focused at or near the free surface of the liquid within the capillary lumen.

5. The apparatus of claim 1 further comprising:
   a coupling fluid positioned between the well plate and the acoustic wave emitter.

6. The apparatus of claim 1 wherein a lower end of the capillary lumen in the well is positioned a distance above a bottom of the reservoir.

7. The apparatus of claim 1 wherein the capillary lumen in the well has an enlarged lower end section.

8. The apparatus of claim 7 wherein the enlarged lower end section varies in diameter and has a maximum diameter at a lower tip.

9. The apparatus of claim 7 wherein the enlarged lower end section expands at an angle between 1 to 70 degrees to an axis extending through the capillary lumen.

10. The apparatus of claim 1 wherein the capillary lumen is cylindrically shaped.

11. The apparatus of claim 1 wherein the capillary lumen is non-cylindrically shaped.

12. The apparatus of claim 1 wherein the capillary lumen is upright.

13. The apparatus of claim 1 wherein the capillary lumen has an inner diameter ranging from 0.1 to 4.0 mm.

14. The apparatus of claim 1 wherein the capillary lumen has a height less than a height of the well such that when a cover is attached atop the well plate, a gap is formed between the capillary lumen and the cover.

15. The apparatus of claim 14 wherein the gap ranges from 1 to 10 mm.

16. The apparatus of claim 2 further comprising:
   a computer which is in communication with the acoustic wave emitter and the translational means, the computer being configured to cause the translational means to align a first capillary lumen in a first well with the acoustic emitter and to cause a first acoustic wave to be emitted from the acoustic wave emitter and into the first capillary lumen to eject a first droplet of liquid out of the first capillary lumen.

17. A liquid dispensing apparatus comprising:
   a well plate comprised of one or more wells, each of the wells having a reservoir and a capillary lumen in fluid communication with the reservoir such that when a liquid is contained in the reservoir, the liquid migrates at least part way up the capillary lumen due to capillary forces; and
   an acoustic wave emitter positioned beneath the well plate, the acoustic wave emitter being configured to emit an acoustic beam that is focused at or near a free surface of the liquid in the capillary lumen, the acoustic beam causing a droplet of the liquid in the capillary lumen of the well to be ejected from the capillary lumen.

18. The apparatus of claim 17 wherein the capillary lumen is cylindrically shaped.

19. The apparatus of claim 18 wherein the capillary lumen has an inner diameter ranging from 0.1 to 4.0 mm.

* * * * *